United States Patent
Endert et al.

(10) Patent No.: US 8,236,770 B2
(45) Date of Patent: Aug. 7, 2012

(54) SERUM-STABLE AMPHOTERIC LIPOSOMES

(75) Inventors: Gerold Endert, Halle (DE); Yvonne Kerwitz, Nordhausen (DE); Monika Fellermeier, Munich (DE)

(73) Assignee: Marina Biotech, Inc., Bothell, WA (US)

(*) Notice: Subject to any disclaimer, the term of this patent is extended or adjusted under 35 U.S.C. 154(b) by 966 days.

(21) Appl. No.: 10/594,553

(22) PCT Filed: Mar. 29, 2005

(86) PCT No.: PCT/DE2005/000589
§ 371 (c)(1),
(2), (4) Date: Sep. 2, 2008

(87) PCT Pub. No.: WO2005/094783
PCT Pub. Date: Oct. 13, 2005

(65) Prior Publication Data
US 2008/0311181 A1    Dec. 18, 2008

(30) Foreign Application Priority Data

Mar. 28, 2004   (DE) .......................... 10 2004 016 020
Nov. 5, 2004    (DE) .......................... 10 2004 054 730

(51) Int. Cl.
| A61K 48/00 | (2006.01) |
| A61K 51/00 | (2006.01) |
| A61K 36/14 | (2006.01) |
| B32B 5/16  | (2006.01) |
| B32B 9/00  | (2006.01) |
| B32B 15/02 | (2006.01) |
| B32B 17/02 | (2006.01) |
| C12N 15/88 | (2006.01) |

(52) U.S. Cl. .................. 514/44 R; 424/1.21; 428/402.2; 435/458; 977/907

(58) Field of Classification Search .................. None
See application file for complete search history.

(56) References Cited

U.S. PATENT DOCUMENTS

| 6,649,780 B1* | 11/2003 | Eibl et al. .................. 554/110 |
| 2005/0164963 A1 | 7/2005 | Essler et al. |
| 2006/0159737 A1* | 7/2006 | Panzner et al. .............. 424/450 |
| 2007/0269504 A1 | 11/2007 | Panzner et al. |

FOREIGN PATENT DOCUMENTS

| WO | WO 02066012 A2 | 8/2002 |
| WO | WO 03070735 A2 | 8/2003 |

OTHER PUBLICATIONS http://www.rockefeller.edu/labheads/tuschl/sirna.html, 7 pages long.*
Budker V et al, "PH-sensitive cationic liposomes: A new synthetic virus-like vector", Bio/technology Nature Publishing Co. New York, US, Bd.14, Jun. 1996, Seiten 760-764, XP002937150.
Leventis R et al, "PH-dependent stability and fusion of liposomes combining protonatable double-chain amphiphiles with phosphatidylethanolamine", Biochemistry American Chemical Society, Easton, PA, US, Bd.26, Nr.12, 1987, Seiten 3267-3276, XP002025621.
Li X J et al, "Theory of Tunable PH-sensitive vesicles of anionic and neutral lipids", Biophysical Journal, New York, US, Bd.80, Nr.1, part 2, Apr. 2001, Seiten 1703-1711, XP008005325.

* cited by examiner

*Primary Examiner* — Robert M Kelly
(74) *Attorney, Agent, or Firm* — Mintz Levin Cohn Ferris Glovsky and Popeo, P.C.; Ivor R. Elrifi; Matthew Pavao

(57) ABSTRACT

The invention relates to amphoteric liposomal formulations which are provided with great serum stability and are suitable for the intracellular delivery of oligonucleotides.

15 Claims, 3 Drawing Sheets

Figure 1:
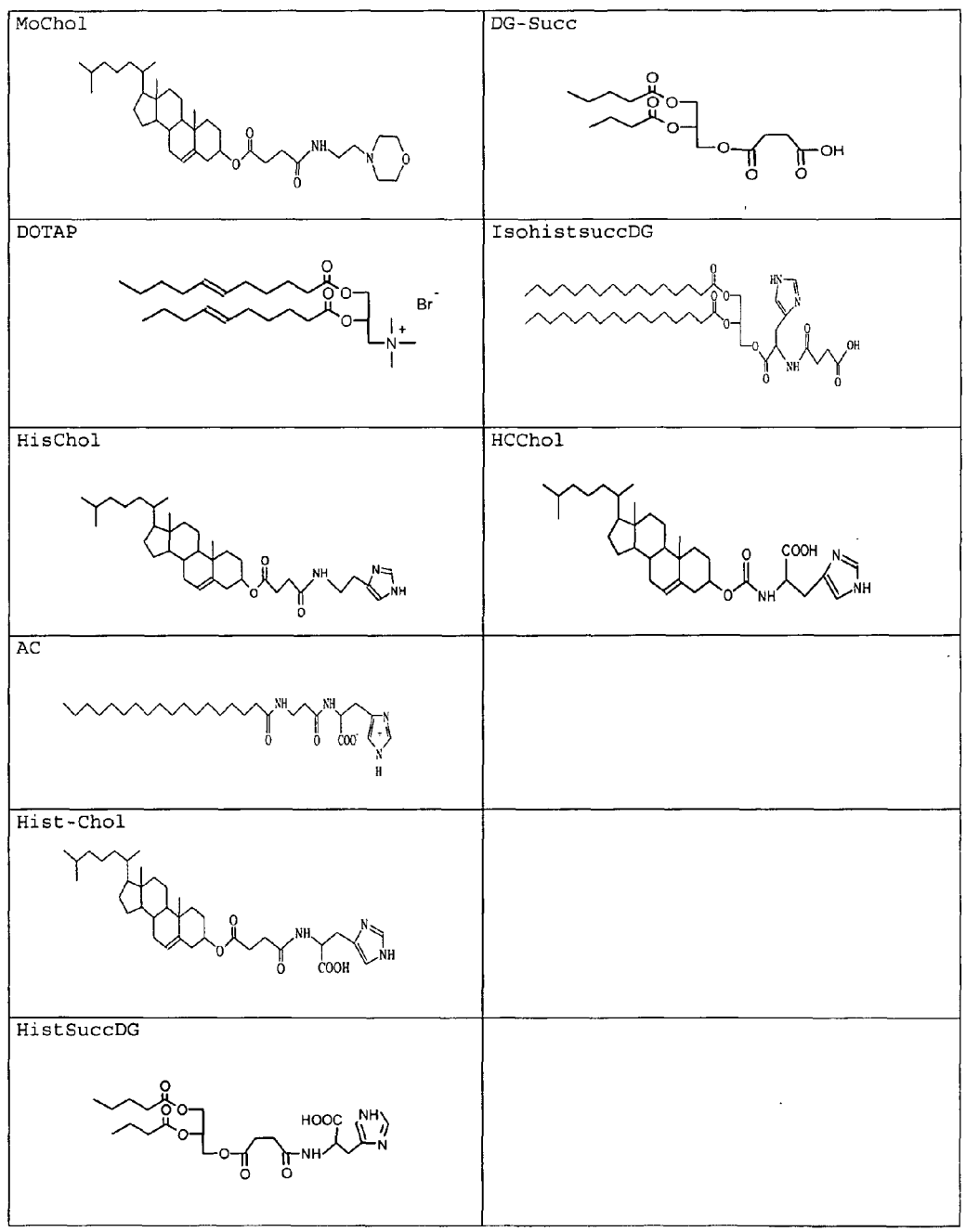

Abbreviations and chemical formulas of lipids used

Figure 2

Pipetting regimen for serum test

|   |        |        | A and B (t = zero) | C to G (in analogy to the other cells) | H (t = 24 h) |
|---|--------|--------|--------------------|----------------------------------------|--------------|
| 1 | Buffer | Basis  | Formulation 1 | | |
| 2 |        | Triton | | | |
| 3 |        | Basis  | Formulation 2 | | |
| 4 |        | Triton | | | |
| 5 |        | Basis  | Formulation 3 | | |
| 6 |        | Triton | | | |
| 7 | Serum  | Basis  | Formulation 1 | | |
| 8 |        | Triton | | | |
| 9 |        | Basis  | Formulation 2 | | |
| 10|        | Triton | | | |
| 11|        | Basis  | Formulation 3 | | |
| 12|        | Triton | | | |

SERUM-STABLE AMPHOTERIC LIPOSOMES

The invention relates to amphoteric liposomal formulations which exhibit unique serum stability and are suitable for the intracellular delivery of oligonucleotides.

The so-called short interfering ribonucleic acids (siRNA) represent a relatively new class of potential pharmaceutical active substances, and they are used in the form of a double strand to downregulate the activity of or switch off particular genes. Unfortunately, their great potential in therapy and diagnostics is accompanied by the disadvantage of marked instability to body fluids. Especially in blood, small nucleic acids undergo very rapid degradation. Attempts are being made to reduce the sensitivity of the nucleic acids by chemical modification of these molecules, but this may frequently result in the disadvantage of reduced to lacking biological activity.

Another approach involves the use of a carrier capable of protecting the siRNA from enzyme attack and transporting it to the site of action. Liposomes have been used as pharmaceutical carriers for drugs for quite some time.

Numerous publications deal with the use of—mostly cationic—liposomal systems for the in vivo intracellular delivery of oligonucleotides (for example, Molecular Membrane Biology, 16, 129-140, (1999); BBA 1464, 251-261, (2000); Reviews in Biology and Biotechnology, 1(2), 27-33, (2001)). However, all these systems involve the common fact that the lipid mixtures used are constituted of unsaturated and cationic lipids such as DOTAP or DOPE and for this reason lack serum stability. As a result, such liposomes will rapidly release the enclosed active substance after parenteral application. Also, complexes of preformed liposomes and nucleic acids (e.g. Lipoplexes) are frequently produced for the applications mentioned above. As a consequence of such complex formation, or of liposomal formulations mostly unstable in serum, stability of the oligonucleotides for a prolonged period of time cannot be guaranteed.

Amphoteric liposomes are a new class of liposomes which, compared to conventional liposomes and purely cationic systems, offer advantageous properties for intracellular delivery. Negatively charged active substances, such as nucleic acids, allow effective packaging in the interior of such liposomes, although the overall charge of the liposomes remains negative at physiological pH. By altering the ambient pH—as encountered during endosomal uptake of liposomes in cells—from neutral to slightly acidic, the charge of the amphoteric liposomes also changes from anionic to slightly cationic, thus utilizing the advantages of a cationic transfection reagent. Such liposomes have been described in WO 02/66012 A2 for the first time. WO 02/66490 and WO 02/66489 (WO 03/070220 and WO 03/070735) present pH-sensitive lipids suitable for the construction of amphoteric liposomes.

Hafez et al. (Biophysical Journal 2000 (79), 1438-46) and Shi et al. (Journal of Controlled Release 2002 (80), 309-319) describe the production of pH-sensitive liposomes formulated without neutral lipids. The liposomes have negative charge at physiological pH values and include pH-sensitive components containing weakly anionic or weakly cationic amphiphiles. The lipids form stable liposomes at neutral or basic pH. In acid medium, the anionic or cationic lipids are protonated, thereby being discharged or recharged. As a result of electrostatic destabilization, the liposomes undergo aggregation more rapidly, promoting membrane fusion. However, liposomes exclusively consisting of charged components are not suitable for in vivo applications due to their low stability in serum.

Apart from standard conditions for parenteral application, such as sterility, isoosmolarity, purity and toxicity requirements, stability and absence of aggregation of a liposomal formulation in human serum are one precondition for successful use in systemic application. Thus, the guidelines of the American FDA regulate specific tests for liposomal formulations (http://www.fda.gov/cder/guidance/index.htm, Liposome Drug Products). Therein, it is demanded that the ratio of encapsulated drug to free drug be determined in vitro as well as in vivo during the circulation time.

Serum components can make the liposomal membrane permeable and liberate active substance. Whether an active substance is released rapidly, slowly, or not at all, also depends on the molecular dimensions of the active substance. Thus, a plasmid having several thousand base pairs will have a higher tendency to remain in the liposome than a small oligonucleotide. For intracellular delivery, it is essential that the release be as low as possible.

Surprisingly, the amphoteric liposomes disclosed in WO 02/66012 A2 were found to differ strongly in their serum stability when using small oligonucleotides. The object of the present invention is therefore to provide formulations of amphoteric liposomes which enclose small oligonucleotides, such as siRNA and/or antisense molecules, in their interior and do not liberate them under serum conditions, or only a small part thereof, thus being suitable for parenteral administration.

The invention achieves said object by providing liposomal formulations with an aqueous interior comprising
neutral lipids with a membrane proportion of 10 to 60 mole-%,
cholesterol with a proportion of 30 to 50 mole-%,
and, as charged lipids, either
amphoteric lipids with a proportion of 5 to 30 mole-%, or
mixtures of cationic and anionic lipids with an overall proportion of 50 mole-% at maximum,
said formulation comprising as active substance at least one oligonucleotide in the aqueous interior.

Oligonucleotides relevant to this embodiment of the invention are constituted of 5-100, preferably 5-40 and more preferably 10-25 nucleotides or base pairs. Moreover, the oligonucleotides can be present as a single strand (e.g. antisense oligonucleotides), double strand (e.g. small interfering RNA, decoy oligonucleotides), or in complex folding (e.g. aptamers, spiegelmers, ribozymes).

All oligonucleotides relevant to this invention are constituted of deoxyribonucleotides or ribonucleotides and chemically modified derivatives thereof, such as phosphorothioate DNA (PS), 2'-O-methyl-RNA (OMe), 2'-O-methoxyethyl-RNA (MOE), peptide nucleic acid (PNA), N3'-P5'-phosphoroamidate (NP), 2'-fluoroarabino nucleic acid (FANA), locked nucleic acid (LNA), morpholinophosphoroamidate (MF), cyclohexene nucleic acid (CeNA), tricyclo-DNA (tcDNA). Moreover, copolymers and block copolymers of various nucleotides and so-called gapmers can be enclosed in the liposomes.

In one advantageous embodiment of the invention, aptamers or spiegelmers are enclosed in the liposomes.

Aptamers are DNA- or RNA-based oligonucleotides with a complex three-dimensional structure. Owing to this structure, aptamers can bind to protein targets with high specificity and high affinity, thus having a therapeutic, mostly extracellular, effect. Their functionality is virtually identical to that of monoclonal antibodies.

Unlike D-oligonucleotides, spiegelmers are constituted of L-ribose and L-2'-deoxyribose units. Just like aptamers, these mirror image nucleic acids specifically bind to protein targets.

Owing to the chiral inversion, spiegelmers—in contrast to conventional D-oligonucleotides—have increased stability with respect to enzymatic degradation.

The basic backbone of the amphoteric liposomes of the invention is constituted of neutral backbone lipids with a proportion in the membrane of 5 to 65 mole-%, preferably 10 to 60 mole-%. Suitable lipids are phoshatidylcholines, such as DMPC, DPPC, DSPC, DOPC and POPC, which can be of both synthetic and natural, or semi-synthetic origin.

It is well-known to those skilled in the art that the serum stability of liposomes can be increased by addition of cholesterol in the membrane. The same has been found for amphoteric liposomes. The liposomes according to the invention preferably have a content of 30 to 50 mole-%, more preferably 35 to 45 mole-% cholesterol in the membrane.

Many lipids that can be used as charge carriers for amphoteric liposomes are derived from the basic chemical structure of cholesterol (for example, the compounds disclosed in WO 02/66490 and WO 02/6648).

Surprisingly, it was found that these cholesterol derivatives, especially MoChol, HisChol, CHEMS, HistChol, generally do not have the stabilizing effect of native cholesterol, for which reason it is advantageous that the sum of all sterol-based lipids does not exceed 60 mole-%.

The amphoteric charge behavior can be generated in two ways: by using amphoteric lipids, or by means of suitable mixtures of pH-sensitive cationic and anionic lipids, such as those disclosed in WO 02/066012. When using amphoteric lipids, the proportion in the membrane is between 5 and 30 mole-%, more preferably between 5 and 20 mole-%, and in mixtures the overall amount of charge carriers is no more than 50 mole-%, more preferably between 15 and 45 mole-%.

In a preferred embodiment of the invention, amphoteric formulations are composed as follows:
  basic lipid selected from the group of DMPC, DPPC, DSPC with 10 to 60 mole-%,
  cholesterol with 35 to 45 mole-%,
  amphoteric lipid selected from the group of HistChol, HistDG, isoHistSuccDG, acylcarnosine, HCChol with 5 to 20 mole-%.

In another preferred embodiment of the invention, formulations are composed as follows:
  basic lipid selected from the group of DMPC, DPPC, DSPC with 10 to 50 mole-%,
  cholesterol with 35 to 45 mole-%,
  mixture of cationic and anionic lipids, at least one being pH-sensitive, selected from the groups of
    a) cationic: DMTAP, DPTAP, DOTAP, DC Chol, MoChol, HisChol, DPIM, CHIM, DORIE, DDAB, DAC Chol, TC Chol, DOTMA, DOGS, $C(18)_2Gly^+$ N,N-dioctadecylamidoglycine, CTAP, CpyC, DODAP and DOEPC with 5 to 40 mole-%;
    b) anionic: DGSucc, DMPS, DPPS, DOPS, POPS, DMPG, DPPG, DOPG, POPG, DMPA, DPPA, DOPA, POPA, Chems and CetylP with 5 to 40 mole-%,
with a proportion in the liposomal membrane of 15 to 45 mole-% in total.

In a particularly preferred embodiment of the invention the formulation and the composition thereof are selected from Table 3.

For use of the formulations according to the invention as drug carriers, it may be convenient to add substances which increase the endurance and serve to regulate the osmotic pressure.

The liposomes according to the invention can be produced according to prior art methods, such as extrusion through membranes of well-defined pore size, ethanol injection or high pressure homogenization. This will be exemplified in the examples.

Non-entrapped active substance is removed. To this end, suitable separation methods are used, so that at least 90% of the active substance is entrapped in the liposome and less than 10% of the active substance is outside the liposome. Chromatographic methods, centrifugation, dialysis or ultrafiltration can be used for this purpose.

The liposomal formulations according to the invention can be used for therapeutic treatment of a mammal. They can also be used for therapeutic treatment of humans.

The liposomal formulations according to the invention are particularly suitable for parenteral application, preferably intravenous application. Accordingly, the invention also relates to a kit comprising the liposomal formulation of the invention, optionally together with a suitable carrier, and to the use of said kit in diagnosis and therapy.

TABLE 1

| No. | Lipid mixture | Ratio | Serum stability |
|---|---|---|---|
| 26 | DMPC/MoChol/DMPS/Cho | 40:10:10:40 | + |
| 12 | DMPC/AC/Chol | 50:10:40 | + |
| 13 | DMPC/HisChol/DPPS/Choi | 35:10:15:40 | + |
| 15 | DMPC/IsoHistSuccDG/Cho | 50:10:40 | + |
| 09 | DMPC/MoChol/DGSucc/Cho | 35:10:15:40 | + |
| 10 | DMPC/MoChol/DGSucc/Cho | 40:10:10:40 | + |
| 11 | POPC/MoChol/DGSucc/ChD | 35:10:15:40 | + |
| 05 | DMPC/HistChol/Chol | 50:10:40 | + |
| 07 | POPC/MoChol/DG-Succ/Chol | 20:10:30:40 | + |
| 02 | DMPC/Hist-DG/Chol/ | 50:10:40 | + |
| 03 | DMPC/MoChol/DG-Succ/Chol | 20:10:30:40 | + |
| 06 | POPC/MoChol/DPPS/Cho | 40:10:10:40 | + |
| 2a | DPPC/DOTAP/DGSucc/Chol | 20:10:30:40 | + |
| 3a | DPPC/HistChol/Chol | 50:10:40 | + |
| 4a | DPPC/HistDG/Chol | 40:20:40 | + |
| 7a | DP PC/MoChol/DGSucc/Chol | 20:10:30:40 | + |
| 4 | DMPC/DOTAP/DG-Succ/Choi | 29:14:43:14 | − |
| 1 | DPPC/DOTAP/Chems/Cho | 50:10:30:10 | − |
| X | DPPC/DOTAP/Chems | 60:10:30 | − |
| Y | POPC/DOTAP/Chems | 60:10:30 | − |
| 6 | DPPC/MoChol/Chems/Chol | 50:10:30:10 | − |
| SC10A | POPC/HcChol/Chol | 50:15:35 | + |
| HC5 | DPPC/HistChol/Chol | 50:15:35 | + |
| SC5 | POPC/HistChol/Chol | 50:15:35 | + |
| HC10A | DPPC/HcChol/Chol | 50:15:35 | + |
| SC1Ea | POPC/HisChol/Chems | 60:20:20 | − |
| SCIS | POPC/HisChol/Chems | 50:15:35 | − |
| HC1Eb | DPPC/HisChol/Chems | 60:20:20 | − |
| HC39 | DPPC/DGSucc/Chems | 50:15:35 | − |
| SC7B | POPC/HistPS/Chol | 50:15:35 | + |
| S7B | POPC/HistPS | 60:40 | − |
| HC7B | DPPC/HistPS/Chol | 50:15:35 | + |
| H7B | DPPC/HistPS | 60:40 | − |
| SC3C | POPO/MoChol/Chems | 50:15:35 | − |
| HC3C | DPPC/MoChol/Chems | 50:15:35 | − |
| SC19B | DPPC/DOTAP/Chems | 50:15:35 | − |
| SC6 | POPC/AC/Chol | 50:15:35 | + |
| S6 | POPC/AC | 60:40 | − |
| HC6 | DPPC/AC/Chol | 50:15:35 | + |
| H6 | DPPC/AC | 60:40 | − |
| HC12 | DPPC/CHIM/Chems | 50:15:35 | − |
| SC12 | POPC/CHIM/Chems | 50:15:35 | − |
| H34 | DPPC/HistSuccDG | 60:40 | − |
| S5 | POPC/HistChol | 60:40 | − |
| SC34 | POPC/HistSuccDG/Cho | 50:15:35 | + |
| HC35 | DPPC/IsoHistSuccDG/Cho | 50:15:35 | + |
| SC35 | POPC/IsoHistSuccDG/Cho | 50:15:35 | + |
| HC34 | DPPC/HistSucc/Chol | 50:15:35 | + |

TABLE 3

| Composition | Molar ratios |
|---|---|
| DMPC/MoChol/DMPS/Chol | 40:10:10:40 |
| DMPC/AC/Chol | 50:10:40 |
| DMPC/HisChol/DPPS/Chol | 35:10:15:40 |
| DMPC/IsohistsuccDG/Chol | 50:10:40 |
| DMPC/MoChol/DG-Succ/Chol | 35:10:15:40 |
| DMPC/MoChol/DG-Succ/Chol | 40:10:10:40 |
| POPC/MoChol/DG-Succ/Chol | 35:10:15:40 |
| DMPC/HistChol/Chol | 50:10:40 |
| POPC/MoChol/DG-Succ/Chol | 20:10:30:40 |
| DMPC/HistSuccDG/Chol/ | 50:10:40 |
| DMPC/MoChol/DG-Succ/Chol | 20:10:30:40 |
| POPC/MoChol/DPPS/Chol | 40:10:10:40 |
| DPPC/DOTAP/DG-Succ/Chol | 20:10:30:40 |
| DPPC/HistChol/Chol | 50:10:40 |
| DPPC/HistSuccChol | 40:20:40 |
| DPPC/MoChol/DG-Succ/Chol | 20:10:30:40 |
| POPC/HcChol/Chol | 50:15:35 |
| DPPC/HcChol/Chol | 50:15:35 |
| POPC/AC/Chol | 50:15:35 |
| DPPC/AC/Chol | 50:15:35 |
| DPPC/HistChol/Chol | 50:15:35 |
| POPC/HistChol/Chol | 50:15:35 |
| POPC/HistSuccDG/Chol | 50:15:35 |
| DPPC/IsoHistSuccDG/Chol | 50:15:35 |
| POPC/IsoHistSuccDG/Chol | 50:15:35 |
| DPPC/HistSuccDG/Chol | 50:15:35 |
| POPC/MoChol/Chems/Chol | 40:10:10:40 |
| POPC/DOTAP/Chems/Chol | 30:10:20:40 |
| DMPC/HisChol/DG-Succ/Chol | 40:10:10:40 |
| POPC/HisChol/Chems/Chol | 40:10:10:40 |
| DMPC/MoChol/Chems/Chol | 40:10:10:40 |
| POPC/MoChol/DG-Succ/Chol | 30:20:10:40 |

Without intending to be limiting, the invention will be explained in more detail with reference to the examples.

| Abbreviations: | |
|---|---|
| DMPC | Dimyristoylphosphatidylcholine |
| DPPC | Dipalmitoylphosphatidylcholine |
| DSPC | Distearoylphosphatidylcholine |
| POPC | Palmitoyloleoylphosphatidylcholine |
| DOPC | Dioleoylphosphatidylcholine |
| DOPG | Dioleoylphosphatidylglycerol |
| POPG | Palmitoyl oleoylphosphatidylglycerol |
| DMPG | Dimyristoylphosphatidylglycerol |
| DPPG | Dipalmitoylphosphatidylglycerol |
| DMPS | Dimyristoylphosphatidylserine |
| DPPS | Dipalmitoylphosphatidylserine |
| DOPS | Dioleoylphosphatidylserine |
| POPS | Palmitoyloleoylphosphatidylserine |
| DMPA | Dimyristoylphosphatidic acid |
| DPPA | Dipalmitoylphosphatidic acid |
| DOPA | Dioleoylphosphatidic acid |
| POPA | Palmitoyloleoylphosphatidic acid |
| DOPE | Dioleoylphosphatidylethanolamine |
| CHEMS | Cholesterol hemisuccinate |
| DC-Chol | 3-β-[N-(N',N'-dimethylethane)carbamoyl]cholesterol |
| CetylP | Cetyl phosphate |
| DODAP | (1,2-dioleoyloxypropyl)-N,N-dimethylammonium chloride |
| DOEPC | 1,2-dioleoyl-sn-glycero-3-ethylphosphocholine |
| DAC-Chol | 3-β-[N-(N,N'-dimethylethane)carbamoyl]cholesterol |
| TC-Chol | 3-β-[N-(N',N',N'-trimethylaminoethane)carbamoyl]cholesterol |
| DOTMA | (1,2-dioleyloxypropyl)-N,N,N-trimethylammonium chloride (Lipo-fectin ®) |
| DOGS | ((C18)₂GlySper3⁺)N,N-dioctadecylamido-glycyl-spermine (Transfectam ®) |
| CTAB | Cetyltrimethylammonium bromide |
| CPyC | Cetylpyridinium chloride |
| DOTAP | (1,2-dioleyloxypropyl)-N,N,N-trimethylammonium salt |
| DMTAP | (1,2-dimyristoyloxypropyl)-N,N,N-trimethylammonium salt |
| DPTAP | (1,2-dipalmitoyloxypropyl)-N,N,N-trimethylammonium salt |
| DOTMA | (1,2-dioleyloxypropyl)-N,N,N-trimethylammonium chloride |
| DORIE | (1,2-dioleyloxypropyl)-3-dimethylhydroxyethylammonium bromide |
| DDAB | Dimethyldioctadecylammonium bromide |
| DPIM | Dipalmitoyl-oxypropyl-methylimidazole |
| CHIM | Histaminyl-cholesterolcarbamate |
| MoChol | 4-(2-Aminoethyl)morpholino-cholesterol hemisuccinate |
| HisChol | Histaminyl-cholesterol hemisuccinate |
| HCChol | Nα-Histidinyl-cholesterolcarbamate |
| HistChol | Nα-Histidinyl-cholesterol hemisuccinate |
| AC | Acylcarnosine, stearyl- & palmitoylcarnosine |
| HistSuccDG | 1,2-Dipalmitoylglycerol hemisuccinate-Nα-histidinyl hemisuccinate, & distearoyl, dimyristoyl, dioleoyl or palmitoyl-oleoyl derivatives |
| IsoHistSuccDG | 1,2-dipalmitoylglycerol-Oα-histidinyl-Nα-hemisuccinate & distearoyl, dimyristoyl, dioleoyl or palmitoyl-oleoyl derivatives |
| DGSucc | 1,2-dipalmitoyglycerol-3-hemisuccinate & distearoyl, dimyristoyl, dioleoyl or palmitoyl-oleoyl derivatives |

FIGURES

FIG. 1: Chemical formulas of lipids

FIG. 2: Array of a 96-well microtiter plate for the serum stability test wherein the liberation of the CF fluorescence marker is measured.

Figure 3:
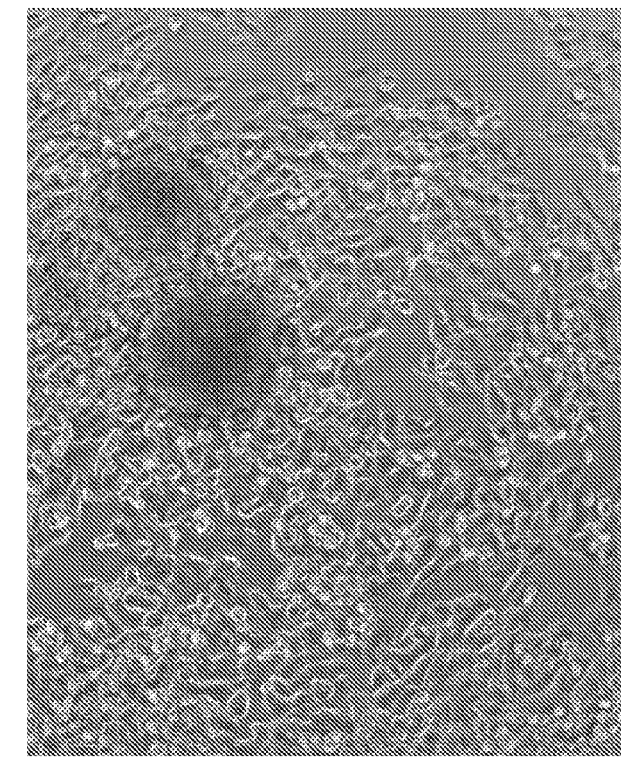
Figure 3:
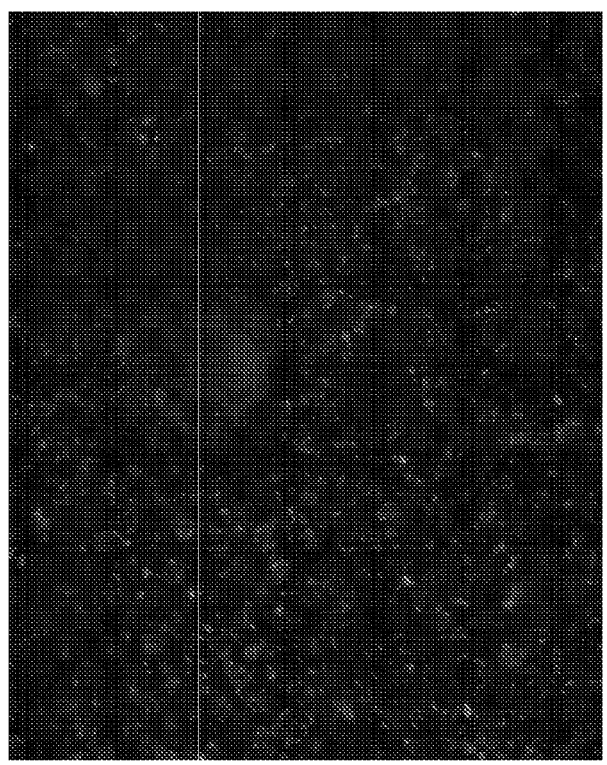

FIG. 3: Fluorescence-microscopic image (panel "A") and phase-contrast micrograph (panel "B") for cell localization.

EXAMPLE 1

Production of Amphoteric Liposomes

A mixture of the lipids specified in Table 1 is dissolved in chloroform at the molar ratios indicated and subsequently dried completely in vacuum in a rotary evaporator.

The lipid film is added with 10 mM HEPES, 150 mM NaCl, pH 7.5, so as to form a 100 mM suspension. Subsequently, this suspension is hydrated in a water bath at 50° C. for 45 minutes with rotating and treated in an ultrasonic bath for another 5 minutes. Thereafter, the suspension is frozen.

Following thawing, the liposomes are subjected to multiple extrusions through a membrane having a pore width of 400 nm.

Liposomes Loaded with CF (Carboxyfluorescein)

The preparation is effected in analogy to the above, with the exception that a solution of the dye is used to hydrate the lipid film: 500 mg of CF is dissolved in 130 µl of 5 M NaCl, 12.5 ml of 10 mM HEPES, pH 7.5, and 630 µl of 5 N NaOH. The pH value is controlled and optionally re-adjusted (to pH 7.5). Removal of non-entrapped CF is effected by gel filtration.

EXAMPLE 2

Inclusion of Cy5.5 Anti-CD40 ODN (Fluorescence-labelled Antisense Oligonucleotide) in Amphoteric Liposomes A lipid mixture having the composition DMPC/MoChol/DG-Succ/Chol 40:10:10:40 (mole-%) is dissolved in chloroform at 50° C. and subsequently dried completely in vacuum in a rotary evaporator.

The lipid film is added with Cy5.5 anti-CD40 ODN (antisense oligonucleotide; 150 µg/ml in 10 mM Na acetate, 300 mM sucrose, pH 4.5) in an amount so as to form a 15 mM suspension. Subsequently, this suspension is hydrated in a water bath at 50° C. for 45 minutes with agitating and treated in an ultrasonic bath for another 5 minutes. Thereafter, the suspension is frozen. This is followed by 3 cycles of freezing and thawing, each thawing being followed by a 5 minute treatment in the ultrasonic bath.

Following final thawing, the liposomes are subjected to multiple extrusions through a membrane having a pore width of 200 nm or 400 nm (Avestin LiposoFast, polycarbonate membrane with a pore width of 200 or 400 nm). Following extrusion, a pH of 7.5 is adjusted by adding a 1 mol/l HEPES stock solution removal of free active substance by triple sedimentation in an ultracentrifuge at 60,000×g for 45 min, the amount of entrapped Cy5.5 anti-CD40 ODN (antisense oligonucleotide) is determined using fluorescence. The oligonucleotide inclusion efficiency is found by determining the lipid content and by fluorimetric Cy5.5 determination as the ratio of lipid and ODN material used and is 53% for the formulation above.

EXAMPLE 3

Determination of Serum Stability

Carboxyfluorescein (CF) is used as a model active substance which, like oligonucleotides, is negatively charged at physiological pH. The serum stability of the CF-loaded liposomes is observed at 37° C. over a period of 24 hours in total. The liberation of CF from the liposomes is observed per fluorescence measurement over the above period of time. Testing of 3 different liposome formulations per 96-well plate is possible. To determine the percentage of liberated CF, the sample incubated in buffer is measured both directly (basis value) and following rupture of the liposomes by addition of Triton (Triton value or 100% value).

Sterile-filtrated serum and 1 mM liposomes are combined in an overall volume of 500 µl. The same batch is prepared with buffer instead of serum as a control.

Prior to each sampling, the 96-well plate is prepared as follows: 5 µl of buffer (10 mM HEPES, 150 mM NaCl, pH 7.5) is placed in each well of a line, columns 1, 3, 5, 7, 9 and 11, and 5 µl of 10% Triton X-100 in each of the columns 2, 4, 6, 8, 10 and 12.

The array of the 96-well plate is as illustrated in FIG. 2. 5 µl of liposomes incubated in buffer is placed in each column 1-6, and liposomes incubated in serum in columns 7-12. 290 µl of buffer is added to the 5 µl of sample plus 5 µl of buffer or Triton. Again, basis and Triton values are taken each time. In this way, it is possible to test three formulations over 8 points in times per plate. The points in time are: zero, zero, 15 min, 30 min, 1 h, 3 h, 5 h, 24 h.

A plate reader with 485/530 nm filters is used for fluorescence measurement. Using the measured fluorescence data, the relative release values are calculated, the Triton value corresponding to 100% release. Table 1 shows a number of tested formulations. It appears that only compositions according to the invention have high serum stability.

EXAMPLE 4

Inclusion of FITC-ODN (Fluorescence-labelled Antisense DNA)

The antisense oligonucleotide (ODN) used herein is an 18-mer phosphorothioate with an FITC label at the 5' end (fluorescein isothiocyanate). Liposomes with FITC-ODN were prepared: 0.5 ml of a 1 mM lipid solution with 9 µg ODN; two batches with different molar ratio of cationic lipid charge to anionic ODN charge, 3:1 and 4.5:1.

DPPC/DOTAP/DG-Succ/Chol 20/10/30/40 each time;
hydration solution or ODN solution: 10 mM NaOAc, pH 4.5, 300 mM sucrose;
to remove non-entrapped ODNs, the liposomes were floated in a discontinuous sucrose gradient with 0, 0.8 and 1.2 M sucrose in Hep$^{10}$, NaCl$^{150}$ (10 mM HEPES, 150 mM NaCl).

Determination of incorporation of FITC-ODN from the sum of measured FITC-ODN fluorescences (100%) and input, respectively, and derived ratio of free to incorporated fluorescence:

| % | Liposomes | Lipo residues | Buffer/Sucrose | Free ODN | Total |
|---|---|---|---|---|---|
| 3:1 | 43.3 | 14.7 | 5.4 | 36.6 | 100.0 |
| 4.5:1 | 46.3 | 10.7 | 4.5 | 38.5 | 100.0 |

EXAMPLE 5

Inclusion of siRNA (Anti-GFP) in Amphoteric Liposomes

The charge ratio of cationic lipid to anionic siRNA is selected to be 5:1 to 10:1. The siRNA (in 10 mM HEPES, 10 mM NaCl pH 7.2) is mixed with hydration buffer (10 mM Na acetate, 10 mM NaCl, 280 mM sucrose, pH 4.5) and placed on the lipid film so as to form a 5-10 mM lipid suspension. The lipids are removed from the flask wall by ultrasonication (10 min at maximum). Hydration is for 15 min at room temperature (POPC as carrier lipid) or at 50° C. (with DMPC, DPPC as carrier lipid). This is followed by freezing at −70° C. (10 min for a 1 ml volume, 30 min for volumes up to 15 ml) and subsequent thawing in a water bath (temperature as in hydration) for at least three times.

The flask is thawed, and, in the event of larger volumes, 3 ml of solution is collected (in 8 ml glass tubes). The residual batch is re-frozen at −70° C.

Extrusion is effected through 100 nm filters. Subsequently, the pH value is adjusted to pH 8.0 using 1/10 volume of 1 M HEPES.

Flotation of the Liposomes:

The liposome fractions are added with the same volume of 2.4 M sucrose in H$_2$O (i.e., a 1.2 M solution is formed). The gradient is layered using buffer (10 mM HEPES, 150 mM NaCl, pH 7.5), 0.8 M sucrose in buffer underneath, and the liposomes in 1.2 M sucrose in H$_2$O at the bottom. The volume of the gradient is 4.5 ml at maximum. Flotation is effected at room temperature in an ultracentrifuge at 50,000 rpm for 45 min. Liposomes situated between the 0.8 M sucrose and buffer layers are collected.

RNA quantification using Ribo Green RNA Quantification Reagent

The assay is performed in a final volume of 200 µl. Initially, an siRNA calibration series between 1 ng and 10 ng (10-100 µl, 100 ng/ml siRNA) is prepared. The Ribo Green is diluted 1:2000 in TE buffer. Each batch is added with 100 µl Ribo Green, followed by incubation for 5 min at room temperature, and the fluorescence at 485/520 nm is measured. Each batch is added with 4 µl of 10% Triton (final concentration: 0.2 mM). This calibration curve can later be used to determine the amount of siRNA entrapped in the liposomes. After about 15 min, the fluorescence is measured once more. The results are plotted in a diagram (one curve with and without Triton each time), and straight calibration lines with the associated equations are generated from these values.

The liposomes are diluted to make two different concentrations (e.g. 1:50 and 1:100), and 2-3 different volumes of the dilutions (e.g. 5, 10 and 15 μl of the dilutions ad 100 μl TE plus 100 μl of Ribo Green reagent) are measured without and with Triton.

The calculated concentration of the siRNA of a formulation must be in rough agreement with the different measurements being made. If this is not the case, the amount of siRNA was outside the calibration curves, and these values should not find entry into the calculation of the concentration. Table 2 shows the efficiency of siRNA incorporation in various formulations.

TABLE 2

Inclusion of siRNA (antiGFP) in amphoteric liposomes

| Formulation | Compositions | Efficiency |
| --- | --- | --- |
| POPC/MoChol/Chems/Chol | 50:10:30:10 | 8.7% |
| DMPC/HistDG/Chol | 50:10:40 | 8.7% |
| DMPC/MoChol/DGSucc/Chol | 20:10:30:40 | 6.1% |
| DMPCIDOTAP/DGSucc/Chol | 20:10:30:40 | 20.5% |
| DMPC/HistChol/Chol | 50:10:40 | 56.4% |
| POPC/MOChol/DPPS/Chol | 40:10:10:40 | 58.4% |
| POPC/MoChol/DGSucc/Chol | 20:10:30:40 | 8.1% |
| DMPC/MOChol/DGSucc/Chol | 35:10:15:40 | 21 |
| POPC/MoChol/DGSucc/Chol | 35:10.15:40 | 16.8% |
| DMPC/AC/Chol | 50:10:40 | 30.4% |
| DMPCIHisChol/DPPS/Chol | 35:10:15:40 | 30.1% |
| DMPC/isoHistSuccDG/Chol | 50:10:40 | 21.1% |
| DMPC/MoChol/DG-Succ/Chol | 40:10:10:40 | 49% |
| DMPC/HisChol/DPPS/Chol | 35:10:15:40 | 46% |

Test of siRNA-containing Liposomes in Serum

Non-modified siRNA undergoes very rapid degradation in serum. The following procedure is used to investigate the protective effect of the liposomes on siRNA. The concentration of entrapped siRNA is determined prior to the serum test. For each test time, liposomes with 4 μg of siRNA are used. Test times: 0, 1 h, 2 h and 4 h.

The liposomes having 4 μg of siRNA incorporated therein are diluted to make a volume of 60 μl, using the buffer which includes the liposomes (usually 10 mM HEPES, 150 mM NaCl, pH 7.5). The batches are added with 60 μl of serum and incubated at 37° C. until the corresponding point in time is reached. The zero time is determined separately.

For good separation of serum components and lipids from siRNA, a phenol/chloroform extraction is performed using PLG Eppis (phase-lock gel Eppendorf tubes). The PLG Eppis are centrifuged at 13,000 rpm for 1 min and placed on ice (the following operations are performed at 4° C. at maximum). The PLG Eppis are added with 280 μl of buffer (as above) and 45 μl of 5 M NaCl. This solution is added with the batch of liposomes in serum (120 μl). Immediately thereafter, 300 μl of a phenol/chloroform mixture is added. For the zero value, 60 μl of serum is also added to the buffer with NaCl in the PLG Eppi. All of the above is mixed immediately.

This is followed by centrifugation at 13,000 rpm and 4° C. for 10 min. The aqueous phase includes the free siRNA. The gradient is added with another 300 μl of chloroform and mixed briefly. After another centrifugation as above, the aqueous phase is clear and can be removed, preferably completely. Next, the siRNA is precipitated from the aqueous phase. The siRNA solution is added with $\frac{1}{10}$ by volume of 3 M NaOAc, pH 5.2, and 2.5 parts by volume ethanol. The solution is mixed thoroughly, and the siRNA is precipitated for 1 h at −70° C. This is followed by another centrifugation at 4° C. and 13,000 rpm for 10 min, thereby pelletizing the siRNA. The supernatant is removed completely, and the pellet is washed with 200 μl of 70% ethanol and dried for about 10 min. The siRNA is redissolved in 5 μl of water.

The quality of the siRNA is examined in a denaturing and optionally in a native acrylamide gel as well.

Detection of siRNA Double-strandedness in Native Acrylamide Gel

The quality of siRNA is defined by the complete length of the single strands and double-strandedness. Using a native acrylamide gel, it is possible to examine the double-strandedness of an siRNA because double-stranded siRNA migrates more slowly in a native gel than single strands.

The gel is pre-eluted with TBE buffer for 30 min (80 V, 100 mA) to achieve the required temperature.

A maximum of 2 μg of siRNA per slot is applied because otherwise the gel would be overloaded. The samples are taken up in a total volume of 90μl. This is added with 1 μl of Blue Juice loading buffer. The samples are applied to the pre-eluted gel and separated for 1 h at 100 mA.

Gel Staining:

Following electrophoresis, the gel is removed from the apparatus. The gel is added with about 200 ml of Stains All solution for use (20 ml of stock solution, 180 ml of formamide, 200 ml of water). The gel is stained in the Stains All solution in the dark for 30-60 min. Thereafter, the solution is removed from the gel, and the gel is destained in water with admission of light (about 30 min to 2 h, depending on the light intensity). The siRNA remains stained, whereas the background is completely destained.

EXAMPLE 6

In vitro Reception of Amphoteric Liposomes with Cy3-BCL2 Antisense in HepG2 Cells HepG2 cells are seeded in 96-well plates 2 days before transfection so as to have a cell density of 60-80% (0.02 to $0.2 \times 10^5$ in 100 μl, normally $1 \times 10^4$) on the day of transfection. Two plates (centrifugation and control incubation) are prepared which otherwise are subjected to identical treatment.

Transfection:

Preheating of centrifuge (Biofuge Stratos, Heraeus), impeller # 3048 for microtiter plates. Cy3-BCL2 antisense-containing liposomes are adjusted to a uniform concentration, using 10 mM HEPES, 150 mM NaCl, pH 7.5 (HBS) (Cy3 is a red-fluorescent label).

Preparation of liposome dilutions (with and without cargo) and transfection mix of commercial control transfection reagents (e.g. Lipofectamine 2000, Oligofectamine, siPort Amine, siPort Lipid) on 96-well plate with serum-free medium (about 160 ng antisense/well). The liposome dilution is added to the cells in a volume of 25-50 μl.

The cells are washed with serum-free medium (1×) and added with serum-containing or serum-free medium, e.g. 75 μl per well, if the liposome dilutions have been produced in such a way that the corresponding quantity of antisense/well is contained in 25 μl.

A multi-well plate is centrifuged at 1500 rpm (342 g), 1 h, 37° C., the control plate is incubated for 1 h (37° C., 5% $CO_2$). Subsequently, both plates are incubated for 3 h (37° C., 5% $CO_2$).

Completely remove medium of all wells, wash 1x with PBS, 2× with serum-containing medium; add serum-containing medium to all wells; microscopic control for vitality, subsequently incubate both plates overnight (37° C., 5% $CO_2$).

On the day following transfection, the reception of liposomes in the cells is investigated using fluorescence microscopy. FIG. 3 illustrates a fluorescence image and a phase-contrast micrograph for cell localization.

EXAMPLE 7

Determination of Serum Stability of Amphoteric Liposomes without and with Cholesterol and/or Matrix Lipid
Inclusion of FITC-dextran in Amphoteric Liposomes The following formulations were prepared with 15 mg/ml FITC-dextran (in 10 mM HEPES, 150 mM NaCl, pH 3.9 (HAc), as in Hafez IM, Ansell S, Cullis PR: Tunable pH-sensitive liposomes composed of mixtures of cationic and anionic lipids. Biophys J. 2000 September; 79(3): 1438-46.).

| | |
|---|---|
| E1 | DC-Chol/DOPA (66/34) |
| E2 | DC-Chol/DOPA/Chol (40/20/40) |
| E3 | DMPC/DC-Chol/DOPA (60/27/13) |
| E4 | DMPC/DC-Chol/DOPA/Chol (20/27/13/40) |
| E5 | DMPC/DC-Chol/DOPA/Chol (30/20/10/40) |
| E6 | DMPC/DC-Chol/DOPA/Chol (40/13/7/40) |

Following extrusion, the liposomes were floated so as to remove the outside FITC-dextran. Using a Zetasizer, the following data were measured at pH 3.9 (10 mM HEPES, 150 mM NaCl, HAc) or pH 9.0 (10 mM Tris, 150 mM NaCl):

| Sample | KCps | ZETA | Z ave[nm] | PI |
|---|---|---|---|---|
| E1 (pH = 3.9) | 1352 | 27.0 ± 3.4 | 215.9 | 0.109 |
| E1 (pH = 9.0) | 1276 | −40.2 ± 0 | 185.2 | 0.126 |
| E2 (pH = 3.9) | 2664 | 28.0 ± 1.0 | 266.5 | 0.162 |
| E2 (pH = 9.0) | 2564 | −38.0 ± 2.9 | 235.5 | 0.177 |
| E3 (pH = 3.9) | 1061 | 24.0 ± 1.6 | 184.8 | 0.128 |
| E3 (pH = 9.0) | 1135 | −11.5 ± 1.2 | 161.6 | 0.109 |
| E4 (pH = 3.9) | 1338 | 21.3 ± 3.3 | 202.6 | 0.081 |
| E4 (pH = 9.0) | 1186 | −24.2 ± 0.6 | 166.6 | 0.122 |
| E5 (pH = 3.9) | 1033 | 21.9 ± 3.8 | 186.8 | 0.102 |
| E5 (pH = 9.0) | 1130 | −14.6 ± 1.9 | 158.1 | 0.089 |
| E6 (pH = 3.9) | 1228 | 11.2 ± 3.3 | 175.1 | 0.141 |
| E6 (pH = 9.0) | 1086 | −10.4 ± 3.3 | 147.3 | 0.093 |

Test of FITC-dextran-containing Liposomes in Serum

To test the stability of these formulations in human serum, ~1 mM liposomes were incubated for 3 hours at 37° C. in human serum and subsequently floated. The fluorescence was determined in the non-floated sample and in the lower layer (serum layer) of the floated sample, and the cargo release was calculated therefrom. The proportion of outside FITC-dextran at the begin of testing was determined in the same way by corresponding dilution in buffer, pH 3.9, and subsequent flotation.

| | % outside at begin of test | % release following serum incubation |
|---|---|---|
| E1 | 13.2 ± 1.2 | 37.0 ± 5.4 |
| E2 | 25.2 ± 1.1 | 52.2 ± 4.2 |
| E3 | 8.6 | 40.4 ± 1.6 |
| E4 | 12.0 | 18.1 ± 0.3 |
| E5 | 12.0 | 21.2 ± 1.6 |
| E6 | 7.6 | 20.0 ± 0.6 |

All those formulations containing both 40% cholesterol and matrix lipid (E4, E5, E6) are more stable than those formulations containing cholesterol only (E2) or matrix lipid only (E3) or none of both (E1).

The invention claimed is:

1. A serum-stable amphoteric liposomal formulation comprising a liposome with an aqueous interior and at least one active substance in the aqueous interior, wherein the liposomes comprise 10-60 mole-% neutral lipids, 30-50 mole-% cholesterol, and, as charged lipids, either 5-30 mole-% amphoteric lipids or a maximum of 50 mole-% of a mixture of cationic and anionic lipids,
and wherein the active substance comprises at least one oligonucleotide.

2. The liposomal formulation according to claim 1, wherein the liposomes comprise 35 to 45 mole-% cholesterol and 5 to 20 mole-% amphoteric lipids.

3. The liposomal formulation according to claim 1, wherein the oligonucleotides comprise deoxyribonucleotides, ribonucleotide or chemically modified derivatives thereof, which are 5-100 bases in length.

4. The liposomal formulation according to claim 1, wherein the oligonucleotides are present as single strands and/or double strands.

5. The liposomal formulation according to claim 4, wherein the oligonucleotide is a small interfering RNA.

6. The liposomal formulation according to claim 1, wherein the oligonucleotide is an antisense oligonucleotide.

7. The liposomal formulation according to claim 1, wherein the oligonucleotide is an aptamer.

8. The liposomal formulation according to claim 1, wherein the oligonucleotide is a spiegelmer.

9. The liposomal formulation according to claim 1, wherein the liposome has a molar composition (in mole-%) selected from the group consisting of:
DMPC/MoChol/DMPS/Chol 40:10:10:40,
DMPC/AC/Chol 50:10:40,
DMPC/HisChol/DPPS/Chol 35:10:15:40,
DMPC/IsohistsuccDG/Chol 50:10:40,
DMPC/MoChol/DGSucc/Chol 35:10:15:40,
DMPC/MoChol/DGSucc/Chol 40:10:10:40,
POPC/MoChol/DGSucc/Chol 35:10:15:40,
DMPC/HistSuccDG/Chol 50:10:40,
POPC/MoChol/DPPS/Chol 40:10:10:40,
DPPC/DOTAP/DGSucc/Chol 20:10:30:40,
DPPC/HistChol/Chol 50:10:40,
DPPC/HistSuccDG/Chol 40:20:40,
DPPC/MoChol/DGSucc/Chol 20:10:30:40,
POPC/HcChol/Chol 50:15:35,
DPPC/HcChol/Chol 50:15:35,
POPC/HistPS/Chol 50:15:35,
DPPC/HistPS/Chol 50:15:35,
POPC/AC/Chol 50:15:35,
DPPC/AC/Chol 50:15:35,
DPPC/HistChol/Chol 50:15:35,
POPC/HistChol/Chol 50:15:35,
DMPC/MoChol/DGSucc/Chol 20:10:30:40,
POPC/HistSuccDG/Chol 50:15:35,
DPPC/IsoHistSuccDG/Chol 50:15:35,
DPPC/HistSuccDG/Chol 50:15:35,
POPC/IsoHistSuccDG/Chol 50:15:35,
DMPC/MoChol/DGSucc/Chol 20:10:30:40,
POPC/MoChol/CHEMS/Chol 40:10:10:40,
DMPC/HistChol/Chol 50:10:40,
POPC/DOTAP/CHEMS/Chol 30:10:20:40,
DMPC/HisChol/DGSucc/Chol 40:10:10:40,
POPC/HisChol/CHEMS/Chol 40:10:10:40,
DMPC/MoChol/CHEMS/Chol 40:10:10:40 and
POPC/MoChol/DGSucc/Chol 30:20:10:40.

10. A method of delivering an oligonucleotide to a mammal comprising administering to the mammal the oligonucleotide in the liposomal formulation of claim 1.

11. The method of claim 10 wherein the mammal is a human.

12. The method of claim 10 wherein the liposomal formulation is administered parenterally.

13. The method of claim 10, wherein the liposomal formulation further includes one or more active substances.

14. The liposomal formulation according to claim 1, wherein the liposomes comprise 35 to 45 mole-% cholesterol and 15 to 45 mole-% of said mixtures of cationic and anionic lipids.

15. The liposomal formulation according to claim 1, wherein the oligonucleotide is a decoy oligonucleotide.

* * * * *